United States Patent [19]

Burd et al.

[11] Patent Number: 5,639,672

[45] Date of Patent: Jun. 17, 1997

[54] ELECTROCHEMICAL DETERMINATION OF FRUCTOSAMINE

[75] Inventors: John F. Burd, San Diego; Gebhard Neyer, Los Angeles, both of Calif.

[73] Assignee: LXN Corporation, San Diego, Calif.

[21] Appl. No.: 543,482

[22] Filed: Oct. 16, 1995

[51] Int. Cl.[6] .................................................. G01N 33/553
[52] U.S. Cl. ........................... 436/525; 436/547; 436/63; 436/111; 436/151; 436/174; 436/806; 436/815; 422/82.01; 435/7.1
[58] Field of Search .................................. 436/525, 547, 436/63, 111, 151, 174, 806, 815; 422/82.01–82.03; 435/7.1

[56] References Cited

U.S. PATENT DOCUMENTS

| | | |
|---|---|---|
| 4,478,744 | 10/1984 | Mezei et al. . |
| 4,511,659 | 4/1985 | Matson ................................ 436/150 |
| 4,545,382 | 10/1985 | Higgins et al. . |
| 4,642,295 | 2/1987 | Baker . |
| 4,645,742 | 2/1987 | Baker . |
| 4,711,245 | 12/1987 | Higgins et al. . |
| 4,806,468 | 2/1989 | Wagner et al. . |
| 4,820,636 | 4/1989 | Hill et al. . |
| 4,837,166 | 6/1989 | de Montigny et al. ................. 436/111 |
| 4,876,205 | 10/1989 | Green et al. . |
| 4,883,057 | 11/1989 | Broderick ............................... 128/631 |
| 4,956,301 | 9/1990 | Ismail et al. . |
| 5,124,253 | 6/1992 | Foulds et al. . |
| 5,183,739 | 2/1993 | Cohen . |
| 5,206,144 | 4/1993 | Zeuthen et al. . |
| 5,264,106 | 11/1993 | McAleer et al. . |
| 5,385,846 | 1/1995 | Kuhn et al. . |
| 5,387,109 | 2/1995 | Ishikawa et al. . |
| 5,470,752 | 11/1995 | Burd et al. ................................ 436/87 |

FOREIGN PATENT DOCUMENTS

| | | |
|---|---|---|
| 0473189A2 | 3/1992 | European Pat. Off. . |
| 0526150A1 | 2/1993 | European Pat. Off. . |
| 0573942A1 | 12/1993 | European Pat. Off. . |
| 0593096A2 | 4/1994 | European Pat. Off. . |
| 61-268178 | 11/1986 | Japan . |
| 3155780 | 7/1991 | Japan . |

OTHER PUBLICATIONS

D.A. Armbuster, "Fructosamine: Structure, Analysis, and Clinical Usefulness," *Clin. Chem.*, 33/12:2153–2163 (1987).

T. Horiuchi et al., "Purification and Properties of Fructosylamine Oxidase from *Aspergillus* sp. 1005", *Agric. Biol. Chem.*, 55(2):333–338 (1991).

C. Gerhardinger et al., "Novel Degradation Pathway of Glycated Amino Acids in Free fructosamine by a *Pseudomonas* sp. Soil Strain Extract", *J. Biol. Chem.*, 270:218–224 (1995).

M. Oimomi et al., "Purification of α-ketoaldehyde Dehydrogenasefrom the Human Liver and its possible Significance from the Human Liver and its Possible Significance in the control fo Glycation", *Experientia*, 45:463–466 (1989).

*Primary Examiner*—James C. Housel
*Assistant Examiner*—Rachel Freed
*Attorney, Agent, or Firm*—Campbell & Flores LLP

[57] ABSTRACT

The present invention relates to a method for electrochemically measuring the concentration of fructosamine, or its high alkalinity eneaminol tautomer in a body fluid sample.

28 Claims, 5 Drawing Sheets

ELECTROCHEMICAL DETERMINATION OF FRUCTOSAMINE

BACKGROUND OF THE INVENTION

1. Field of the Invention

This invention relates to an assay system for determining the glycemic condition of a diabetic. More specifically, it relates to electrochemically measuring the fructosamine concentration in a patient's body fluid sample.

2. Background Information

Individuals suffering from diabetes mellitus have an abnormally high blood sugar level generally because the pancreas does not secrete sufficient amounts of the active hormone insulin into the bloodstream to regulate carbohydrate metabolism. If an abnormally high blood sugar level, known as a hyperglycemic condition, is allowed to continue for prolonged periods, the individual will suffer from the chronic complications of diabetes, including retinopathy, nephropathy, neuropathy and cardiovascular disease. Studies indicate that diabetic patients who are able to maintain near normal glycemic control greatly reduce the likelihood of these dire complications. Therefore, several tests have been developed to measure and monitor glycemic condition.

One common medical test to monitor glycemic condition is the direct measurement of blood glucose levels by diabetics. Because blood glucose levels fluctuate significantly throughout a given day, being influenced by diet, activity, and treatment, depending on the nature and severity of the individual case, some patients measure their blood glucose levels up to seven times a day. Based on the observed pattern in the measured glucose levels, the patient and physician together make adjustments in diet, exercise and insulin intake to better manage the disease. Clearly, this information should be available to the patient immediately.

However, because of the frequent fluctuation of glucose levels in a given day, tests which are independent of a patient's diet, activity, and/or treatment and which provide longer term indications of blood glucose levels have also been developed. These tests include the determination of glucose bound to proteins.

Proteins, such as those present in whole blood, serum and other biological fluids react with glucose, under non-enzymatic conditions, to produce glycated proteins, also known as fructosamine. The extent of the reaction is directly dependent upon the glucose concentration of the blood. Consequently, diabetics usually have an elevated fructosamine concentration compared to a healthy individual. Therefore, the concentration of glycated serum proteins has been used as an indicator of a hyperglycemic condition. In particular, measurement of fructosamine levels is useful for monitoring diabetic control because fructosamine concentration reflects an average of serum glucose levels over a period of time, approximately a half month period.

Fructosamines are formed as follows. The blood proteins, such as serum albumin, are glycated in vivo by a non-enzymatic condensation reaction between glucose and available amino groups of blood proteins, principally the $\epsilon$-amino groups of lysine residues and the $\alpha$-amino groups of the protein's terminal amino acid. The glucose binds to an amino group of the protein to form a Schiff base, i.e., a glycosylamine or aldimine. The glycosylamine undergoes a molecular rearrangement, specifically an Amadori rearrangement, to form a stable ketoamine, termed "fructosamine." This reaction sequence is illustrated in FIG. 1a. Once formed, the stable ketoamine structure remains with the protein throughout its lifespan.

A particularly useful property of fructosamine is that, under basic conditions, it is in equilibrium with its eneaminol tautomer, also termed the fructosamine eneaminol tautomer. This equilibrium conversion is set forth in FIG. 1b. The eneaminol tautomer is a reducing agent. See, for example, Burd et al., U.S. Pat. Nos. 5,740,752, issued Nov. 28, 1995, and Ismail, 4,956,301, Sep. 11, 1990, both of which are incorporated herein by reference. It is the reducing properties of fructosamine and its tautomer that lends itself to one aspect of the instant invention and the electrochemical determination of fructosamine. Oxidation of the eneaminol tautomer yields glucosone and deglycated protein, as is further set forth in FIG. 1c.

Several methods for measuring fructosamine by means other than electrochemical determination are already known. For example, Baker, in U.S. Pat. Nos. 4,642,295 and 4,645,742, discloses methods for determining fructosamine levels in a solution assay. These types of assays have several practical limitations, such as inconvenience associated with solution assays and the need for relatively large volumes of liquid sample. Such methods have been adapted to dry-phase chemistry, for example by Ismail, as disclosed in U.S. Pat. No. 4,956,301. However, Ismail's dry-phase assay is a test-strip device, which requires the use of a reaction accelerator compound. The disclosed accelerator compounds are incapable of performing with certain reagents which are especially useful in fructosamine assays, namely Nitro blue tetrazolium chloride (NBT) and carbonate buffer. Multi-layer test devices for determining fructosamine concentration are also known in the art. For example, Sakamoto, in the published European Patent Application Publication No. 0 473 189, describes a multi-layer analytical element for assaying fructosamine. Staniford et al., in European Patent Application Publication No. 526,150, discuss an enzymatic method comprising pretreatment of a fructosamine-containing sample with a protease then reacting the sample with ketoamine oxidase and measuring the results colormetrically. Modrovich et al., in European Patent Application No. 573,942, detect fructosamine colorimetrically with a tetrazolium salt, using a subtraction method that employed an additional reaction wherein the sample was treated with boric acid to block the oxidation of fructosamine.

One report describes the electrochemical determination of a fructosamine-like compound, glycosylated hemoglobin (HbAlc), using glucose oxidase and a metallocene boronic acid as a mediator. When HbAlc is present, it reacts with metallocene boronic acid to prevent reaction between this metallocene mediator and reduced glucose oxidase. Ishikawa et al., U.S. Pat. No. 5,387,109, describes in the main the colormetric determination of fructosamine using the enzyme fructosylamine deglycase. Ishikawa et al. briefly mentions detecting the $H_2O_2/O_2$ reaction products of the enzyme-catalyzed reaction with specialized $H_2O_2$ and $O_2$ electrodes, respectively, but such electrodes are much more inconvenient to use than the instant biosensors that detect fructosamine, enzymes and mediators.

Most of the methods discussed above employ colorimetric methods of detection. With colorimetric determination there is frequently interference from the natural color of the sample or the precipitate. For example, the red blood cells from a patient's blood sample can interfere with colorimetric determination. Moreover, the volume of sample frequently required with the above-described assays for a proper determination is typically a significant amount. There is a need for a fructosamine assay which has no interference from color or precipitate and which can be used with relatively small sample volumes. Moreover, there is a need for a fast and convenient assay for measuring fructosamine in many types of body fluid samples. Finally, it is desirable to have an assay which involves relatively simple instrumentation and which, preferably, can be miniaturized. The present invention satisfies these needs and provides related advantages as well.

SUMMARY OF THE INVENTION

The present invention relates to a method for electrochemically determining the concentration of a fructosamine in a body fluid sample of a patient. This is ascertained by contacting said body fluid sample with a buffering agent and a biosensor, which is comprised of an anode and a cathode. A voltage is applied between the anode and the electrical current passing between the anode and cathode is measured. The amount of current measured is compared to a standard curve of current versus concentration of fructosamine, as determined for said body fluid. The buffering agent adjusts the pH of body fluid sample to between about 10 to about 12.5. The buffering agent may be on the biosensor or otherwise added to the sample before the current is measured.

Additionally, electrochemical determination of the concentration of a fructosamine in a body fluid sample of a patient can be ascertained by contacting the body fluid sample with one or more mediators, a buffering agent and a biosensor comprised of an anode and cathode. A voltage is applied between the anode and the cathode and the electrical current passing between the anode and cathode is measured. The amount of current measured is compared to a standard curve of current versus concentration of fructosamine, as determined for said body fluid. The buffering agent and mediators are on the biosensor or otherwise added to the sample before said current is measured. The buffering agent adjusts the pH of the body fluid sample to between 4 to about 12.5.

Electrochemical determination of the concentration of a fructosamine in a body fluid sample of a patient can further be ascertained by contacting the body fluid sample with one or more fructosamine-specific oxidoreductase enzymes, a buffering agent and a biosensor comprised of an anode and cathode. A voltage is applied between the anode and cathode and the electrical current passing between the anode and cathode is measured. The amount of current measured is compared to a standard curve of current versus concentration of fructosamine, as determined for said body fluid. The buffering agent and enzyme are on the biosensor or otherwise added to the sample before said current is measured. The buffering agent adjusts the pH of the body fluid sample to between 4 to about 10.

DETAILED DESCRIPTION OF THE INVENTION

Figure 1A:
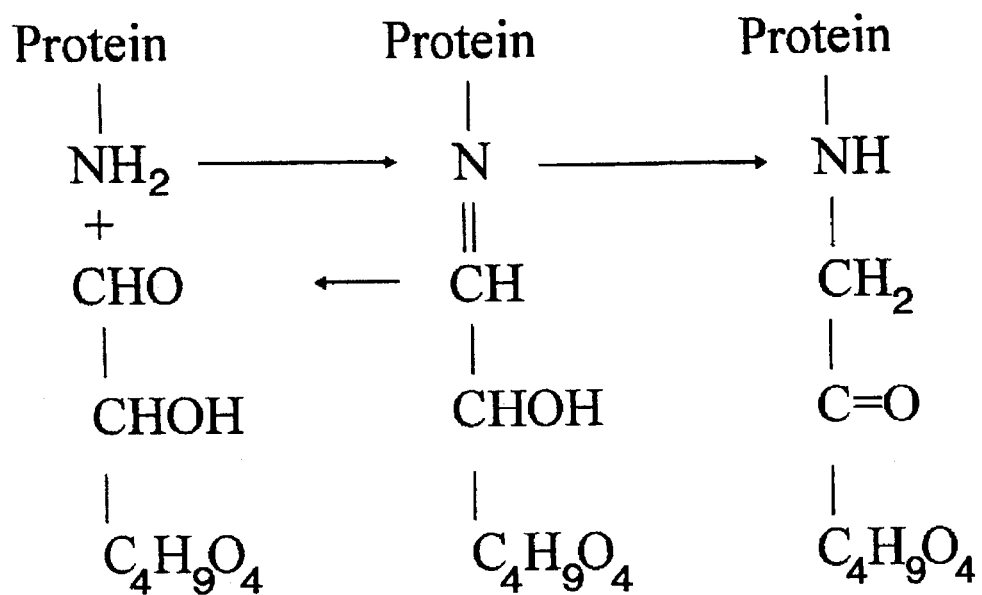
FIG. 1a diagrams the condensation of a protein and glucose to form a glycosylamine and the subsequent Amadori rearrangement to a fructosamine.
Figure 1B:
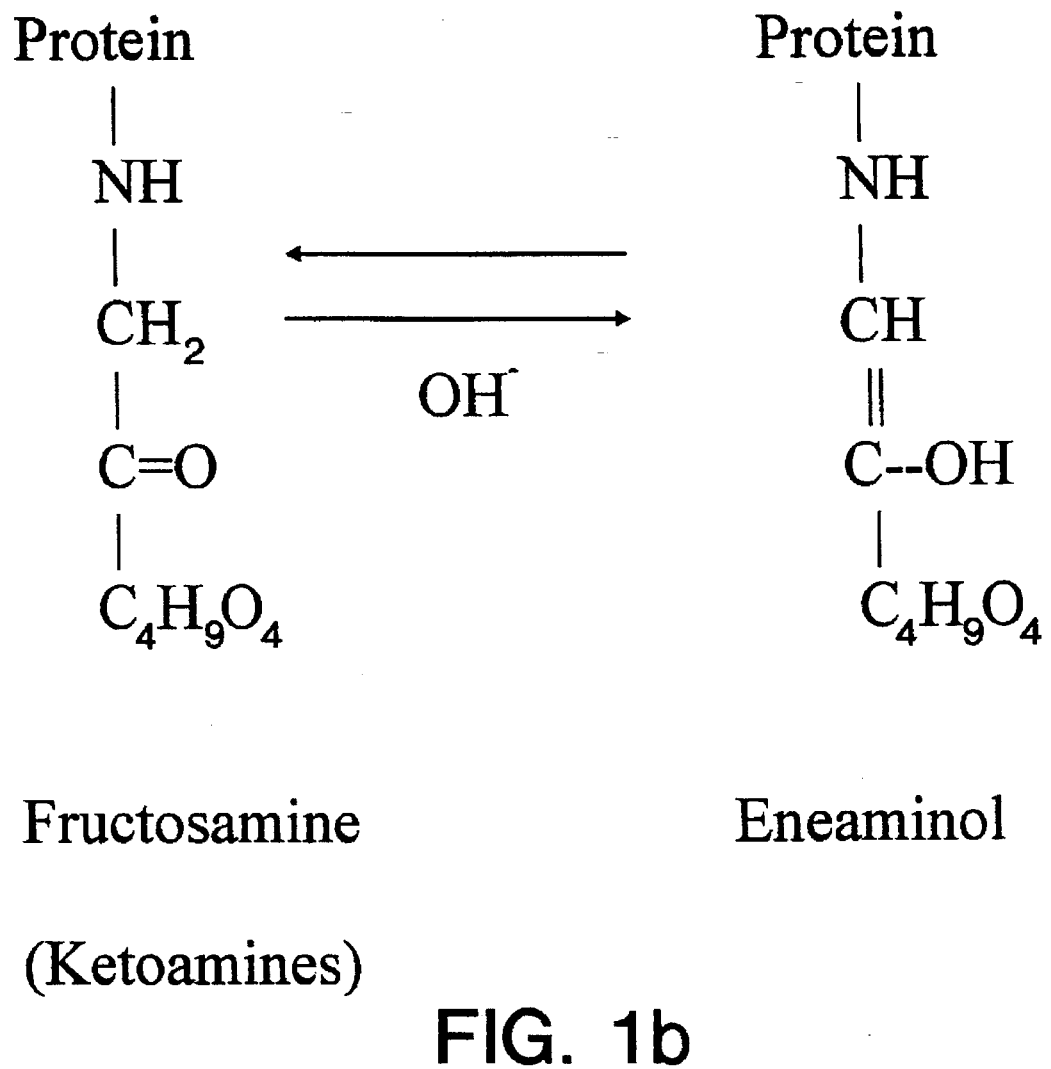
FIG. 1b diagrams the alkaline equilibrium between a fructosamine and its eneaminol tautomer.
Figure 1C:
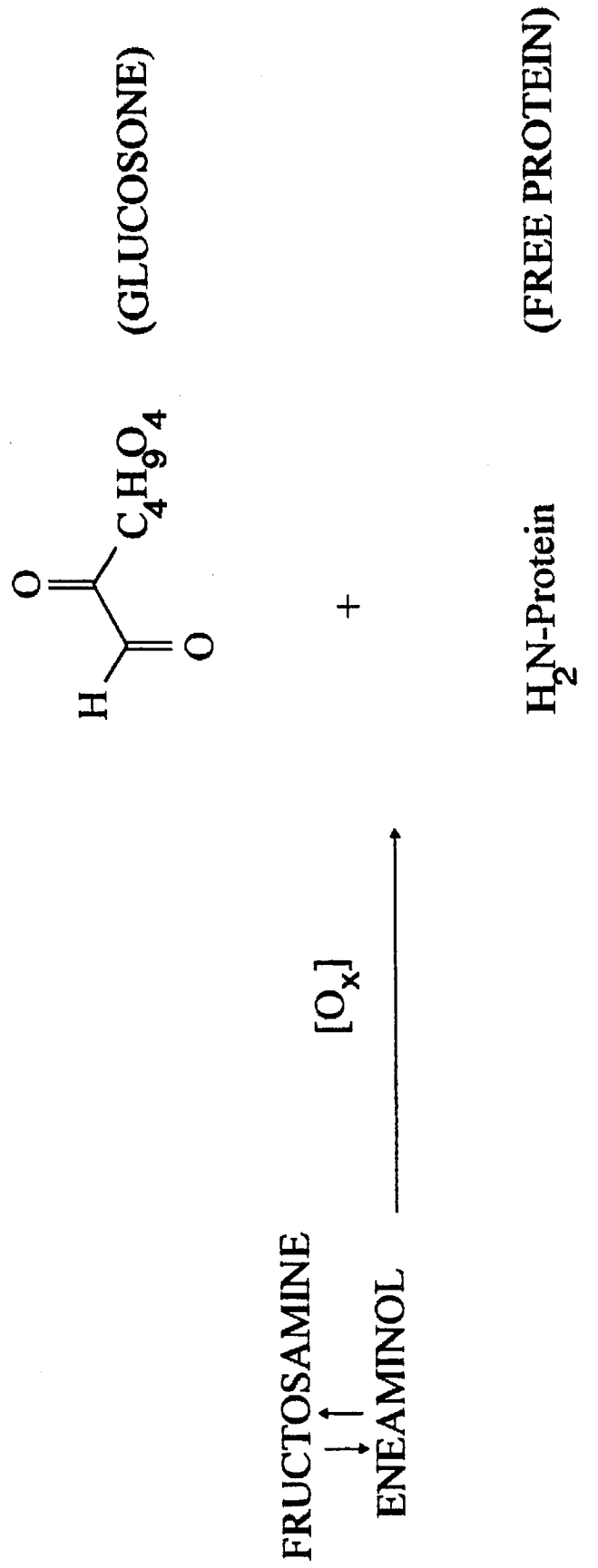
FIG. 1c diagrams one type of oxidation reaction of a fructosamine or eneaminol, resulting in glucosone and a free protein.

This invention involves determining the glucose level in mammalian blood by electrochemically measuring the amount of fructosamine (also called "ketoamines")(FIG. 1a), or its high-alkalinity tautomer, termed an "eneaminol" (FIG. 1b), present in the patient sample. The invention affords in one aspect the convenience of directly measuring, at alkaline pH, the concentration of eneaminol present, and in another aspect the added sensitivity of utilizing mediators in conjunction with the measurement over a wide pH range. Alternatively, such sensitivity and convenience can be achieved with the invention in the pH range of from about 4 to about 10 using oxidoreductase enzymes and, optionally, mediators or co-factors.

More specifically, the electrochemical technique used in the instant bioanalytical invention is known as amperometry. This technique involves measuring the current passed at a fixed voltage. The voltage is fixed in the instant case by the oxidation voltage of fructosamine and its eneaminol tautomer, which are strong reducing agents, or mediators that accept electrons either from fructosamine or its tautomer, or from enzymes oxidizing, or assisting in the oxidation of, fructosamine or its tautomer, wherein said enzymes are optionally used in the presence of a mediator or co-factor.

Figure 2:
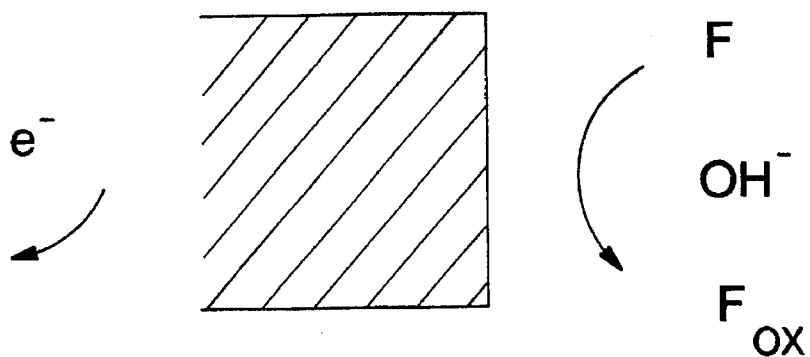
FIG. 2 depicts schematically the oxidation of fructosamine ("F") or the eneaminol tautomer at the anode (shaded area).

One aspect of the instant invention involves the direct electrochemical detection of fructosamine, and more particularly, its alkaline eneaminol tautomer form (FIG. 2). Thus, the body fluid sample is brought into contact with a solid buffering agent (on the surface of the biosensor) or a buffer solution (added to the body fluid sample) in order to bring the pH of resulting solution from between about 10 to about 12.5, and preferably about 10.3 to about 11.5. The buffering agent used should not contain oxidizable groups. Suitable buffering agents include CAPS(3-(cyclohexylamine)-1-propane sulfuric acid, Sigma Chemical, St. Louis, Mo.); sodium hydrogen phosphate/sodium hydroxide; guanadinium salts such as guanadinium carbonate and guanadinium phosphate; potassium chloride/sodium hydroxide; potassium hydrogen phosphate; methanolic sodium hydroxide; tetramethylammonium hydroxide; sodium carbonate/sodium bicarbonate; certain amino acids; and other suitable buffers as are well known in the art; or a combination thereof. The buffering agent can be dried onto a porous mesh surrounding the anode (and any meshes surrounding other electrodes) in order that the agent may be dissolved into the body fluid sample on contact.

A variation of the direct detection of fructosamine entails running a control cell wherein the electroreactivity of the fructosamine in the body fluid sample is blocked using boric acid or one or more boronic acid derivatives, discussed below.

Body fluids often contain substances that can be oxidized at a similar pH and voltage as fructosamine. Such substances include uric acid and ascorbic acid. In the situation where such interference does arise, an additional oxidation can be performed on a portion of the body fluid sample using fructosamine binding agents known in the art to block the oxidation of fructosamine. For instance, boric acid can be added to a portion of the sample itself in conjunction with the use of a porous mesh on a biosensor. In an identical anode half-cell the current passed is measured in the same manner as the untreated anolyte or sample. The current value from the treated anolyte or sample is subtracted from the current value of the untreated one to measure the concentration of fructosamine. The accuracy of this method is assured in that the fructosamine which is present in whole blood and related body fluids is normally present in the largest concentration of any boronic acid—or boric acid-binding compounds subject to reduction at pH of 10 to 12.5. The use of boric acid in non-electrochemical analysis is described in I. E. Modrovich, European Patent Application Publication No. 573,942, published Dec. 15, 1993, herein incorporated by reference. Alternatively, metallocene boronic acids, or other boronic acid derivatives, as discussed in Hill et al., U.S. Pat. No. 4,820,636, issued Apr. 11, 1989, herein incorporated by reference, can be in the same manner as boric acid in order to provide a suitable control method.

Alternatively, fructosamine binding agents can be antibodies against epitopes of fructosamine, which can increase the accuracy of the instant invention. Such antibodies are exemplified in U.S. Pat. Nos. 4,478,744 to Mezer, 4,806,468 to Wagner et al., 5,183,739 to Cohen and 5,206,144 to Zeuthen et al., each of which is incorporated herein by reference.

The concentration of fructosamine or the eneaminol tautomer can be measured indirectly, that is to say, by measuring the concentration of a substance that accepts electrons from fructosamine or the eneaminol which in turn is oxidized at the anode. These substances can afford a reduction in the voltage or the pH of the assay, among other advantages.

Figure 3:
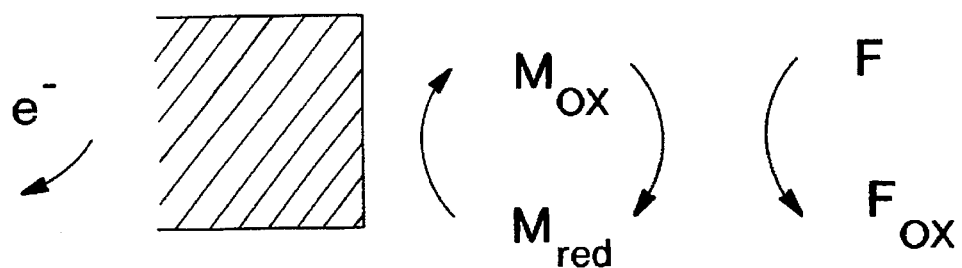
FIG. 3 depicts schematically the oxidation of fructosamine ("F") or the eneaminol tautomer, using a mediator compound ("M") at the anode (shaded area).

One method of indirect measurement involves the use of organic or organometallic molecules, termed mediators (FIG. 3). When not used with the enzymes described below, these mediators are used to facilitate measurement of the oxidation of the eneaminol tautomer. Mediators are electroactive compounds that lower the voltage of the cell needed to conduct the fructosamine oxidation. Such compounds can be coated directly on the electrode, added to the anolyte containing the body fluid sample, or dried on an optional porous mesh surrounding the electrode. Examples of these compounds are well known in the art and include phenazine ethosulfate, phenazine methosulfate, phenylenediamine, 1-methoxyphenazine methosulfate, 2,6-dimethyl-1,4-benzoquinone, 2,5-dichloro-1,4-benzoquinone, 2,6-dichloro-1,4-benzoquinone, chloranil, fluoranil, bromanil, tetrathiafulvalenes (TTF), tetracyanoquinodomethane (TCNQ), a polyviologen, ferrocene, a substituted ferrocene such as 1,1'-ferrocene dicarboxylic acid, 1,1'-dimethylferrocene, vinylferrocene, 2-hydroxyethylferrocene, chloromethyltrimethylaminoferrocene, 1,1-bis (hydroxymethyl) ferrocene, cytochrome C3, benzoquinone, phenylenediamine, soluble transition metal organic complexes as ruthenium or osmium (bipyridyl), (1,10-phenanthrolyl) or (terpyridyl) complexes (e.g., [Ru(bipy)$_3$Cl$_2$]). Discussion of such mediators can be found, for example, in Higgins et al., U.S. Pat. No. 4,545,382, issued Oct. 8, 1985, herein incorporated by reference. In addition, the electrode can be coated with a conduction polymeric material such as poly(aniline), poly(pyrole), or poly (thiophene).

Tetrazolium compounds can also be used as mediators. Ideally, the tetrazolium compound is added to the body fluid sample at a pH between about 10 to 10.8, with the preferred pH being around 10.3. (Maintaining the pH of the body fluid sample/anolyte lower than 12 prevents the tetrazolium compound from reacting with any glucose present in the sample.) The tetrazolium compounds are reduced by the fructosamine present in the sample to give a formazan. The oxidation of the formazan is then measured at the anode.

Suitable tetrazolium compounds for use in this invention are those that are known to react with fructosamine. Such compounds include neotetrazolium chloride (NT), tetranitro blue tetrazolium chloride (TNBT), blue tetrazolium chloride (BT), iodonitrotetrazoilum chloride, nitro blue tetrazolium chloride (NBT), nitro blue monotetrazolium chloride, thiazolyl blue tetrazolium bromide (MTT), tetrazolium violet, 2,3,5-triphenyl-2-H-tetrazolium chloride, thiocarbamyl nitro blue tetrazolium chloride (TCNBT), tetrazolium XTT (XTT), 2-2'-benzothiazolyl-5-styryl-3-(4'-phthalhydrazidyl) tetrazolium chloride (BSPT), and distyryl nitro blue tetrazolium chloride (DSNBT). The preferred compound is nitro blue tetrazolium (NBT).

The tetrazolium compounds should be available in concentrations of about 1 to 30 millimolar in the anolyte or in body fluid sample brought in contact with the biosensor. Further discussion of the conditions for using tetrazolium compounds for the colormetric measurement of fructosamine, (as opposed to the instant electrochemical measure), can be found in D. A. Armbuster, *Clin. Chem.*, 33/12 pp. 2153–2163 (1987)), and the references listed therein.

Preferred mediators include those chosen from the group consisting of ferrocene, a nitro blue tetrazolium salt, a tris [bipyridyl] ruthenium complex or a tris [bipyridyl] osmium complex. Further preferred mediators are ferrocene and nitro blue tetrazolium.

Figure 4:
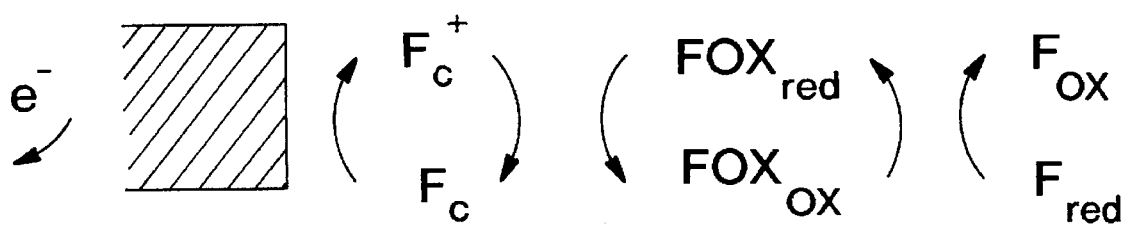
FIG. 4 depicts schematically the oxidation of fructosamine ("F") using both a oxidoreductase enzyme ("FOX") and ferrocene ($F_c$), a mediator compound, at the anode (shaded area).

An alternative aspect of the indirect method of measuring fructosamine or the eneaminol tautomer is the use of oxidoreductase enzymes, with or without the above-mentioned mediators (FIG. 4). Thus, when enzymes alone are used, depending on the enzyme, the concentration of the reduced enzyme, the reaction products of the enzyme-catalyzed reaction, or any co-enzymes needed for the enzyme catalyzed reaction can be measured. Illustrative of the concept is a system employing a combination of pre-treatment with a proteinase and then reaction with ketoamine oxidase, which is described in J. M. Staniford et al., European Patent Application No. 526,150, published Feb. 3, 1993, herein incorporated by reference. Ketoamine oxidase selectively cleaves the fructosyl bond to the protein nitrogen, yielding glucosone; the (unglycated) protein and hydrogen peroxide. Thus, one could electrochemically measure the concentration of the glucosone, the reduced ketoamine oxidase enzyme, or hydrogen peroxide, the latter with a hydrogen peroxide electrode known in the art. Another example would be the use of fructosamine dehydrogenase. In the dehydrogenase reaction, NAD accepts the electrons from the fructosamine oxidized by the enzyme. Thus, in addition to the reduced enzyme and the oxidized fructosamine molecule (glucosone), the concentration of the coenzyme NADH could also be electrochemically measured at the anode. FAD (flavine adenine dinucleotide) is another co-enzyme that could be used with the indirect method.

Glucosone is also generated at alkaline pH by the presence of transition metal ions, such as copper(II) ions. Thus, one skilled in the art could substitute copper(II) ion for the oxidoreductase enzymes in the above indirect procedure and electrochemically measure the concentration of glucosone so generated.

As one skilled in the art would recognize, other enzymes could be used for this indirect method. Such enzymes include the ones described in Japanese Patent No. 30155780; Japanese Patent No. 61-268-178; T. Horiuchi et al., "Purification and Properties of Fructosylamine Oxidase from Aspergillus sp. 1005", *Agric. Diol. Chem.*, 55(2):333–338 (1991); C. Gerhardinger et al., "Novel Degradation Pathway of Glycated Amino Acids into Free Fructosamine by a Pseudomonas sp. Soil Strain Extract", *J. Biol. Chem.*, 270:218–224 (1995); and M. Oimomi et al., "Purification of α-ketoaldehyde Dehydrogenase from the Human Liver and its possible Significance in the Control of Glycation", *Experientia*, 45:463–466 (1989). Particularly preferred is fructosyl oxidase and fructosyl N-alkyl amino acid oxidase.

As one skilled in art would recognize, the pH of the indirect methods utilizing enzymes will be in a lower range than either the direct method or the indirect method utilizing mediators alone. Thus, the enzyme-assisted reactions are preferably run in the pH of between about 6 to about 9. All the other conditions as discussed above are applicable. Thus, for example, the enzyme could be added to the anolyte of the electrochemical cell, to the body fluid sample to be used with a biosensor, or in a dried form on the electrode or on a mesh surrounding the electrode. The concentrations required of such enzymes can be found in the art.

Finally, the mediators can be combined with the enzymes in the indirect method. This combination would be most advantageous when it was necessary to measure the concentration of reduced enzymes (such as fructosamine oxidoreductase) or an unstable reaction product (such as hydrogen peroxide), as both types of substances are generally difficult to measure. Thus, for example, ferrocene is oxidized to ferrocinium ion at the anode, which then is reduced by the reduced form of fructosamine oxidoreductase, the latter having previously oxidized fructosamine. All of the above-listed mediators save for the tetrazolium compounds would function in a manner similar to ferrocene. An example of combinations of a mediator and an enzyme to measure glucose can be found in Higgins et al., U.S. Pat. No. 4,711,245.

The apparatus used in the instant invention can be a conventional electrochemical cell or a smaller form of an electrochemical cell commonly referred to as a "biosensor." The term "biosensor" means the same as that term as used in the art, in other words, wherein at least one anode and one cathode are contained on an insulating support such that as little as one drop (i.e., not more than about 10 microliters) of patient sample will make contact with both the anode and cathode. The difference between a biosensor and a conventional electrochemical cell is mainly the physical size of the anode and cathode, the size, or complete absence of, an anolyte or catholyte, respectively, and the amount of the fluid sample to be measured. Regardless of the type of apparatus used, the electrodes must be connected both to an electrical power supply and a device for measuring both the applied voltage between the electrodes and the amount of current generated from the oxidation of fructosamine and its tautomer at the anode. As it is the oxidation of fructosamine or the tautomer that is directly or indirectly measured, the anode is the working electrode for the instant invention. A third electrode, also called a reference electrode, may optionally be used to help monitor the progress of other reactions at the anode.

Finally, a further option is to use a fourth or auxiliary electrode, which is a second anode, set at a different, usually lower, voltage than the working electrode. The auxiliary electrode can be used to oxidize interfering substances (such as uric acid).

This invention is carried out by electrochemical cells and biosensors in which the composition and shape of the electrodes, and, if applicable, electrolyte cell dividers and porus meshes surrounding the electrodes, are known in the electrochemical and bioanalytical art. Particularly useful textbooks include *Organic Electrochemistry*, M. M. Baizer, Editor, Marcel Dekler, Inc., New York (1973) and *Biosensor Fundamentals and Applications*, Turner, Karube and Wilson, editors, OUP (1987), both of which are incorporated by reference. In addition, further teaching about cells and biosensors suitable for the instant invention can be found in McAleer et al., U.S. Pat. Nos. 5,264,106, issued Nov. 23, 1993; Green et al., 4,876,205, issued Oct. 24, 1989; Higgins et al., 4,545,382, issued Oct. 8, 1985; Foulds et al., 5,124, 253, issued Jun. 23, 1992; Hill et al., 4,820,636, issued Apr. 11, 1989; Kuhn et al., 5,385,846, issued Jan. 31, 1995; and N. G. Carter et al., European Patent Application No. 593, 096, published Apr. 20, 1994, all of which are herein incorporated by reference.

Anodes for use in this invention are, for example, made of glassy carbon, carbon paste, carbon felt, graphite, graphite felt, pyrolytic graphite, mercury, copper, lead, zinc, platinum, silver, gold, titanium or cadmium, or a carbonaceous material coated with a catalytic layer of transition metal. Preferably, the anode is made from a transition metal or a form of carbon, and more preferably, gold, platinum or glassy carbon. The anode material should be rather highly purified, as is normally the case in this art.

The cathode can be made of any purified material which is not attacked by the reductive side of the fructosamine oxidation. Cathodes for this invention are usually made of noble metals, especially platinum, or of other commonly used electrode material, such as carbon. A platinum electrode is the preferred cathode.

The reference electrode, if used, is generally one of known standard voltage. Such an electrode can be a mercury/mercury chloride (saturated calomel, or SCE) or silver/silver chloride electrode, the latter of which is preferred.

The forms of the electrodes used in the current invention are not critical; they may be the same or different and may be a solid sheet, rod, film, gauze or cloth, impermeable or porous microparticles, or a fluidized bed of particles, with equally good results.

It is most effective to arrange the electrodes such that the distance between the anode and cathode, and the other electrodes, if present, are as small as possible, without having the half reactions occurring at each electrode interfering with the corresponding half reaction at the other electrodes. In a biosensor configuration, it is desirable to span the anode and cathode without additional fluid, such that the use of only a drop or two of body fluid sample (e.g., blood, plasma, serum, saliva or urine) is necessary. In general, a close physical proximity is desirable to minimize current flow and minimize the temperature rise caused by the resistance of the body fluid sample to the flow of current.

The voltage between the cathode and the anode may be controlled in various ways. The most effective and precise way to control the voltage is by use of a reference electrode. The desired voltage for the process is determined from the examination of a voltammogram of the system, and the voltage between the cathode and the anode is adjusted to give the desired constant voltage between the reference electrode and the cathode. This method of control is much more effective than control by the overall voltage between the cathode and the anode, since such voltage depends on the condition of the dividing membrane, concentration of the catholyte as well as the concentration of the fructosamine compound to be detected. The current changes can then be monitored at a fixed voltage preferably by measuring the current time (I-t) transient at a suitable voltage against a cathode electrode. A suitable voltage range is from about 200 to about 1100 millivolts, 1000 to 1100 millivolts being preferred, against a silver/silver chloride reference cathode for the direct methods set forth below, and from about 100 mV tp 1000 mV for the assisted methods.

The electrochemical sensor for use in this invention can be one which involves amperometric detection, and one which utilizes a strip element, especially a disposable dry strip. Accordingly the sensor electrodes can comprise electrode areas formed for instance by screen printing, spraying, or other suitable deposition technique.

The dry strip sensor can comprise an elongated, electrically-insulating substrate having a pair of longitudinal, substantially parallel, electrically-conducting tracks thereupon, each track being provided at the same end with means for electrical connection to a read-out means and provided with an anode and cathode additional electrodes may be present, as discussed herein.

More especially, such a sensor is suitably configured in the form of a supporting strip of electrically insulating material such as a synthetic polymer (for instance, pvc) carrying at a location between its ends the two electrodes supported on electrically conductive printed tracks. For example, the electrodes can take the form of two rectangular areas side by side on the strip. Such areas can be configured as a target area to be covered by a single drop of body fluid sample, for testing for the concentration of fructosamine. If desired, non-rectangular electrode areas, for instance diamond-shaped, semicircular, or triangular areas, can be employed to provide a target area for optimized contact by a liquid sample.

Furthermore, a third electrode similar to the anode electrode may be present on the supporting strip. Such an auxiliary electrode can lead to more reliable results, in that if a lower voltage is applied at the auxiliary electrode, the current passed between the latter electrode and the cathode can be subtracted from the current passed at the anode, then the resulting current is due to the oxidation of fructosamine.

In a typical manufacturing procedure of a biosensor, an adhesive can be screen printed or otherwise applied around the sample target area of each strip biosensor followed by placement and adhesion over this area of paper coated with a mediator, co-factor and/or enzyme, if present. A protective porous mesh coated with buffer can be positioned over the sample target layer and held in place by an insulation print applied generally to the test element in order to leave uncoated both the sample target area and terminal ends to be inserted in to a read-out device. The mesh can be polymer, for example, nylon or polyester. The buffer impregnated thereon is discussed above.

The following example is intended to illustrate but limit not the invention.

EXAMPLE I

Direct Determination of Fructosamine

Figure 5:
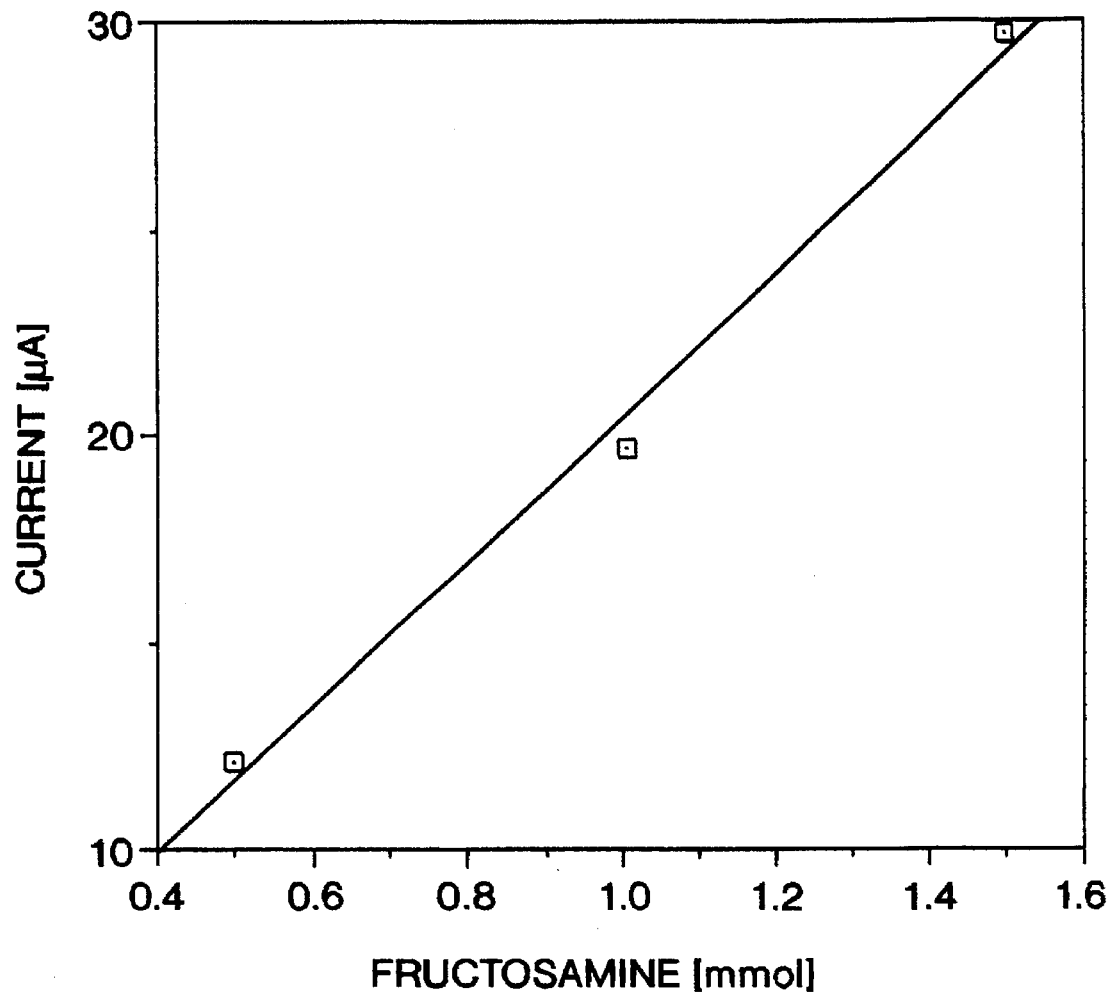
FIG. 5 depicts the results obtained in Example I below. The three data points are for the 0.5, 1.0 and 1.5 mM solutions of glycated human serum albumin, referred to as "fructosamine" on the abscissa of the graph.

Glycated Human Serum Albumin (gHSA) was dissolved in 1M Guanidinium carbonate (pH 11.5) to give 0.5, 1.0 and 1.5 mM solutions. The voltage of these solutions was scanned linearly from −100 mV to +1200 mV, at which point the direction was reversed, scanning back to −100 mV. A 3 mm glassy carbon working electrode together with a Ag/AgCl reference electrode and a platinum auxiliary electrode were used. Oxidation of the gHSA occurred at +1040 mV and the corresponding current was measured as represented by for the dose-response curve in FIG. 5.

Although the invention has been described with reference to the disclosed embodiments, those skilled in the art will readily appreciate that the specific examples detailed are only illustrative of the invention. It should be understood that various modifications can be made without departing from the spirit of the invention. Accordingly, the invention is limited only by the following claims.

We claim:

1. A method for electrochemically determining the concentration of a fructosamine in a body fluid sample of a patient comprising the steps of:
   a. contacting said body fluid sample with a buffering agent and a biosensor, said biosensor comprising an anode and a cathode;
   b. applying a voltage to the anode;
   c. measuring the electrical current passing between the anode and cathode; and
   d. comparing the amount of current measured to a standard curve of current versus concentration of fructosamine, as determined for said body fluid in order to determine the concentration of the fructosamine in said body fluid;

wherein said buffering agent adjusts the pH of body fluid sample to between about 10 to about 12.5, and said buffering agent may be on the biosensor or otherwise added to the sample before the current is measured.

2. A method of claim 1, wherein the anode comprises a transition metal or a form of carbon.

3. A method of claim 2, wherein the anode is glassy carbon, platinum, or gold.

4. A method of claim 1, wherein the pH of the anolyte is adjusted to a pH of about 10.5 to about 11.5.

5. A method of claim 1, further comprising contacting a reference electrode simultaneously with the body fluid sample and measuring the voltage between the reference electrode and the anode.

6. A method of claim 5, wherein the reference electrode is a silver/silver chloride electrode.

7. A method of claim 1, additionally comprising:
   a. contacting the body fluid sample with a second biosensor, said second biosensor utilizing the same buffering agent, anode and cathode as said biosensor;
   b. contacting said body fluid sample with a fructosamine binding agent;
   c. applying the identical voltage to the second anode;
   d. additionally measuring the current between the anode and cathode of the second biosensor;
   e. subtracting the current measured by the second biosensor from that measured for the other biosensor; and
   f. comparing the difference of the two values to said standard curve;

wherein said fructosamine binding agent may be on the biosensor or otherwise added to said sample before the current is measured.

8. A method of claim 7, wherein the fructosamine binding agent is boric acid, one or more boronic acid derivatives, or one or more anti-(fructosamine) antibodies.

9. A method for electrochemically determining the concentration of a fructosamine in a body fluid sample of a patient, comprising the steps of:
   a. contacting the body fluid sample with one or more mediators, a buffering agent and a biosensor comprised of an anode and cathode;
   b. applying a voltage to the anode;
   c. measuring the electrical current passing between the anode and cathode; and
   d. comparing the amount of current measured to a standard curve of current versus concentration of fructosamine in the presence of said one or more mediators, as determined for said body fluid;

wherein said buffering agent and mediator are on the biosensor or otherwise added to the sample before said current is measured; and said buffering agent adjusts the pH of said body fluid sample to between about 4 to about 12.5.

10. A method of claim 9, wherein the mediator is chosen from the group consisting of ferrocene, a nitro blue tetrazolium salt, a tris ruthenium complex, or a tris osmium complex.

11. A method of claim 10, wherein the anode comprises a transition metal or a form of carbon.

12. A method of claim 11, wherein the anode is glassy carbon, platinum, or gold.

13. A method of claim 9, wherein the pH of the body fluid sample is adjusted to a pH of about 10.5 to about 11.5.

14. A method of claim 9, additionally comprising contacting the body fluid sample with a reference electrode and measuring the voltage between the reference electrode and the anode.

15. A method of claim 14, wherein the reference electrode is a silver/silver chloride electrode.

16. A method of claim 10, wherein the mediator is a nitro blue tetrazolium salt and the pH is about 10.3.

17. A method of claim 10, wherein the mediator is ferrocene.

18. A method of claim 9, additionally comprising:
   a. contacting the body fluid sample with a second biosensor, said second biosensor utilizing the same buffering agent, anode and cathode as said biosensor;
   b. contacting said body fluid sample with a fructosamine binding agent;
   c. applying the identical voltage to the second anode;
   d. additionally measuring the current between the anode and cathode of the second biosensor;
   e. subtracting the current measured by the second biosensor from that measured for the other biosensor; and
   f. comparing the difference of the two values to said standard curve;

wherein said fructosamine binding agent may be on the biosensor or otherwise added to said sample before the current is measured.

19. A method of claim 18, wherein the fructosamine binding agent is boric acid, one or more boronic acid derivatives, or one or more anti-(fructosamine) antibodies.

20. A method for electrochemically determining the concentration of a fructosamine in a body fluid sample of a patient, comprising the steps of:
   a. contacting the body fluid sample with an oxidoreductase enzyme, a buffering agent and a biosensor comprised of an anode and cathode;
   b. applying a voltage to the anode;
   c. measuring the electrical current passing between the anode and cathode; and
   d. comparing the amount of current measured to a standard curve of current versus concentration of fructosamine in the presence of said oxidoreductase enzyme, as determined for said body fluid;

wherein said buffering agent and enzyme are on the biosensor or otherwise added to the sample before said current is measured; and said buffering agent adjusts the pH of said body fluid sample to between about 4 to about 10.

21. A method of claim 20, additionally comprising contacting said body fluid sample with one or more mediators or factors, wherein said mediators is initially on the biosensor or otherwise is added to said sample before said current is measured.

22. A method of claim 20 or 21, wherein said enzyme is fructosyl N-alkyl amino acid oxidase or fructosylamine oxidase.

23. A method of claim 21, wherein said one or mediators or cofactors is ferrocene, nitro blue tetrazolium, a tris ruthenium complex, or a tris osmium complex.

24. A method of claim 21, wherein said mediators or cofactors are nicotinamide adenine dinucleotide or flavin adenine dinucleotide.

25. A method of claim 20, wherein the anode comprises a transition metal or a form of carbon.

26. A method of claim 25, wherein the anode is glassy carbon, platinum or gold.

27. A method of claim 20, further comprising simultaneously contacting said body fluid sample with a reference electrode and measuring the voltage between the reference electrode and the anode.

28. A method of claim 27, wherein said reference electrode is a silver/silver chloride electrode.

* * * * *

UNITED STATES PATENT AND TRADEMARK OFFICE
CERTIFICATE OF CORRECTION

PATENT NO. : 5,639,672
DATED : June 17, 1997
INVENTOR(S) : Burd et al.

It is certified that error appears in the above-identified patent and that said Letters Patent is hereby corrected as shown below:

Column 7,
Line 9, please delete "Diol." and replace therefor --Biol.--.

Column 11, Claim 10,
Line 20, please insert -- (bipyridyl) -- after "tris" and before "ruthenium" and after "tris" and before "osmium".

Column 12, Claim 23,
Lines 35 and 36, please insert -- (bipyridyl) -- after "tris" and before "ruthenium" and after "tris" and before "osmium".

Signed and Sealed this

Seventeenth Day of July, 2001

*Attest:*

NICHOLAS P. GODICI
*Attesting Officer*    *Acting Director of the United States Patent and Trademark Office*